United States Patent
Kovacs (10) Patent No.: US 12,150,818 B2
(45) Date of Patent: Nov. 26, 2024

(54) EXPANDABLE CARRIAGE WITH ADJUSTABLE CROSS NUT

(71) Applicant: Innovative Medical Products, Inc., Plainville, CT (US)

(72) Inventor: Tamas Kovacs, Burlington, CT (US)

(73) Assignee: Innovative Medical Products, Inc., Plainville, CT (US)

( * ) Notice: Subject to any disclaimer, the term of this patent is extended or adjusted under 35 U.S.C. 154(b) by 945 days.

(21) Appl. No.: 17/187,759

(22) Filed: Feb. 27, 2021

(65) Prior Publication Data

US 2022/0273392 A1 Sep. 1, 2022

(51) Int. Cl.
| | |
|---|---|
| *E02B 3/00* | (2006.01) |
| *A61B 90/14* | (2016.01) |
| *A61B 90/57* | (2016.01) |
| *A61G 13/10* | (2006.01) |
| *A61G 13/12* | (2006.01) |
| *F16B 2/06* | (2006.01) |
| *A61B 90/50* | (2016.01) |

(52) U.S. Cl.
CPC ............. *A61B 90/14* (2016.02); *A61B 90/57* (2016.02); *A61G 13/101* (2013.01); *A61G 13/1205* (2013.01); *A61G 13/1285* (2013.01); *F16B 2/065* (2013.01); *A61B 2090/508* (2016.02); *A61B 2090/571* (2016.02); *A61B 2560/04* (2013.01)

(58) Field of Classification Search
CPC ... A61B 90/14; A61B 90/57; A61B 2090/508; A61B 2090/571; A61B 2560/04; A61G 13/101; A61G 13/1205; A61G 13/1285; A61G 13/1245; F16B 2/065
See application file for complete search history.

(56) References Cited

U.S. PATENT DOCUMENTS

| | | | |
|---|---|---|---|
| 4,232,681 A | 11/1980 | Tulaszewski | |
| 4,437,791 A * | 3/1984 | Reynolds | E21B 17/01 405/224.2 |
| 4,492,005 A * | 1/1985 | Begley | F16L 3/1075 24/270 |
| 6,058,534 A | 5/2000 | Navarro et al. | |
| 9,603,765 B2 | 3/2017 | Kreuzer et al. | |
| 9,615,987 B2 | 4/2017 | Worm et al. | |
| 10,508,668 B2 * | 12/2019 | Ikushima | F16B 2/10 |
| 11,703,171 B2 * | 7/2023 | Hinton | F16L 23/06 285/312 |

(Continued)

*Primary Examiner* — Amy J. Sterling
(74) *Attorney, Agent, or Firm* — Wasserbauer Law, LLC; Damian G. Wasserbauer, Esq.; Nicholas E. Blanton, Esq.

(57) ABSTRACT

An apparatus for adjustably positioning an extremity or body part such as knees, hands, or feet for a surgical procedure comprising a carriage including a base adapted to engage a track for selective positioning there along, an arm configured to pivotably attach to the base, and a socket formed by the joining of the base and arm, the socket configured to accept a ball of an extremity holder. The apparatus further comprises a clamping assembly and an adjustable cross nut assembly. The adjustable cross nut assembly provides clocking and/or adjustable positioning of an internal thread start to provide optimal positioning of the handle that achieves the clamping effect, as the threads are subject to wear and plastic deformation due to use over time.

14 Claims, 10 Drawing Sheets

(56) References Cited

U.S. PATENT DOCUMENTS

| | | | |
|---|---|---|---|
| 2006/0197344 A1* | 9/2006 | Henry | F16L 23/10 |
| | | | 285/420 |
| 2018/0073528 A1* | 3/2018 | Pryor | F16B 2/065 |
| 2019/0339037 A1* | 11/2019 | Burton | F41A 23/06 |
| 2022/0362084 A1* | 11/2022 | Kovacs | A61F 5/3776 |
| 2023/0151834 A1* | 5/2023 | Kovacs | F16B 5/0072 |
| | | | 361/825 |
| 2023/0338218 A1* | 10/2023 | Kovacs | A61B 90/57 |

\* cited by examiner

EXPANDABLE CARRIAGE WITH ADJUSTABLE CROSS NUT

FIELD OF THE INVENTION

This invention relates to an apparatus of the type used for the positive positioning of a body part for surgical procedures and other medical activities where the body part must be maintained in the selected optimum position with respect to an operating room table. In particular, this invention relates to a patient positioning apparatus positionable by one hand, having improved holding characteristics and sterilization features.

BACKGROUND OF THE INVENTION

Surgical procedures increasingly require precise and predictable positioning of the joint, limb, or other body part corresponding to the surgical site. Optimal positioning requires a large range of easily available positive positioning adjustments, so that the limb, joint, or other body part can be precisely positioned and thereafter maintained in that desired position. While precisely-maintainable positioning is important, so too is the ability to release and reposition the limb, joint, or other body part on demand during the course of the procedure. Therefore, an apparatus, system, and method that provides maintainable, releasable, and repositionable positive positioning ensures optimal access to surgical sites, which require a variety of angular relationships for effective surgery.

Medical devices, including surgical equipment for holding a body part that have contact with body tissues or fluids are considered critical items. These items need to be sterile when used, because any microbial contamination could result in disease transmission. If these items are heat resistant, the recommended sterilization process is steam sterilization, because it has the largest margin of safety due to its reliability, consistency, and lethality. Most medical and surgical devices used in healthcare facilities are made of materials that are heat stable and therefore undergo heat, primarily steam, sterilization. Sterilization destroys all microorganisms on the surface of an article or in a fluid to prevent disease transmission associated with the use of that item. Sterilization refers to any process that eliminates, removes and/or kills all forms of life, including transmissible agents such as fungi, bacteria, viruses, spore forms, etc., present on a surface, which can be achieved by applying heat, chemicals, irradiation, high pressure, and filtration or combinations thereof. The concept of what constitutes "sterile" is measured as a probability of sterility for each item to be sterilized. This probability is commonly referred to as the sterility assurance level (SAL).

Sterilization facilities, such as Sterile Processing Departments (SPDs) are located separately from operating rooms, as these facilities perform heat sterilization on surgical equipment in an autoclave (sometimes called a converter). If, however, sterilization is needed in the operating room, flash sterilization methods are used; for example, should the surgical apparatus become unsterile for some reason, then flash sterilization methods require placing the item in hot liquids to remove pathogens. After flash sterilization occurs, the surgical apparatus may take longer to cool down and reach the required room-temperature, which, in turn, delays the surgical procedure and adds cost.

Problems in sterilizing surgical equipment for holding a limb, joint, or other body part abound. Disadvantages of known surgical equipment include the costs associated with sterilization, whereby nooks and folds where residues accumulate and cannot be, or require increased effort to be, dislodged. Another design problem is in use of multiple parts, whereby the entire set of complex rails, tubes and other parts of the surgical equipment and apparatus required disassembly, scrubbing, power washing and other procedures that increased the cost of the sterilization and overall procedure. In addition, parts of the surgical equipment for holding a limb, joint, or other body part could get lost, or removal may void warranties. In general, such surgical equipment requires sterilization before entering an operating room. Once the surgical procedure ends, the surgical equipment again requires sterilization.

Another design problem involves the wear of clamping components associated with a surgical apparatus as it is used over time. In the field of this invention, a clamping assembly typically achieves a clamping effect by way of external and internal threads, such as a screw-type assembly. The wearing of clamping components has been shown to be particularly prevalent for these threaded components.

Figure 1A:
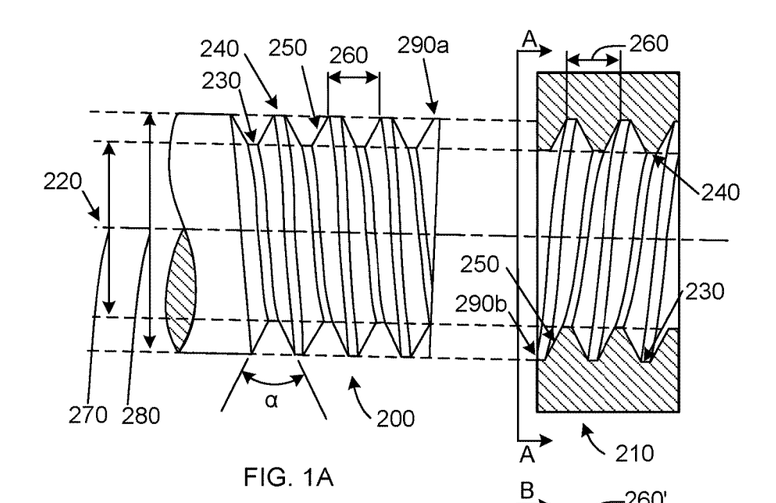
FIG. 1A illustrates a schematic view of a single-start screw-type assembly exhibiting no signs of wear, in accordance with an embodiment of the present invention.
Figure 1B:
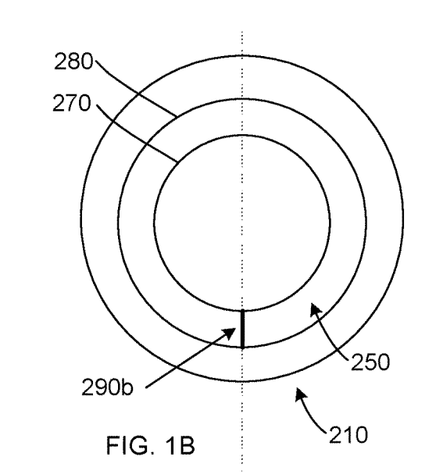
FIG. 1B illustrates a schematic sectional view of the single-start screw-type assembly of FIG. 1A, taken along section A-A, in accordance with an embodiment of the present invention.

FIGS. 1A and 1B provide schematic views of an illustrative screw-type assembly that exhibits no signs of wear in its present condition. FIG. 1B is a schematic sectional view of FIG. 1A, taken along section A-A. The illustrative schematic of FIGS. 1A and 1B show a new, unworn screw-type assembly includes external threads 200 and internal threads 210 that run along a common axis 220. External and internal threads 200, 210 may be characterized by convention thread geometry including, but not necessarily limited to, a root 230, a crest 240, a flank 250, a pitch 260, a minor diameter 270, a major diameter 280, and a thread angle $\alpha$. As defined here, one or more of these parameters are shared by the external and internal thread components 200, 210, albeit subject to any tolerance(s) that allow proper coupling of the screw-type system. Of particular importance to the present application are external start 290a and internal start 290b. As shown in FIG. 1B, internal start 290b is defined at a first radial position; upon threading external threads 200 into internal threads 210, external start 290a will meet internal start 290b at the first radial position to commence the threading process.

Figure 1C:
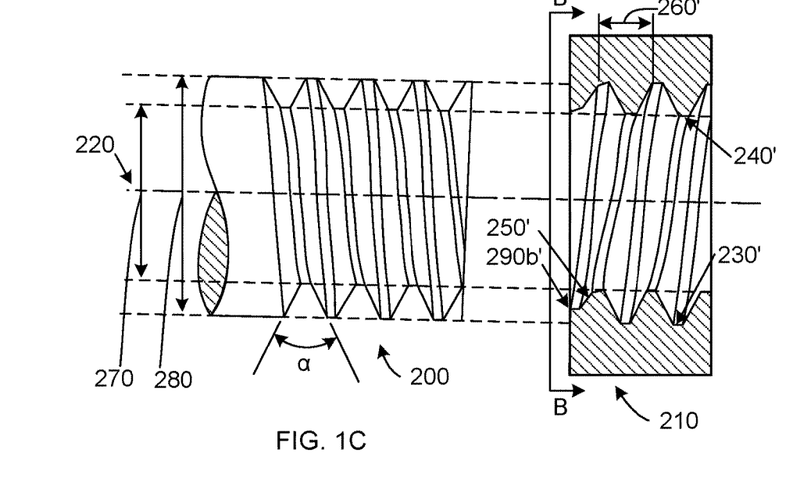
FIG. 1C illustrates a schematic view of a single-start thread design, which has undergone plastic deformation resulting from wear, in accordance with an embodiment of the present invention.
Figure 1D:
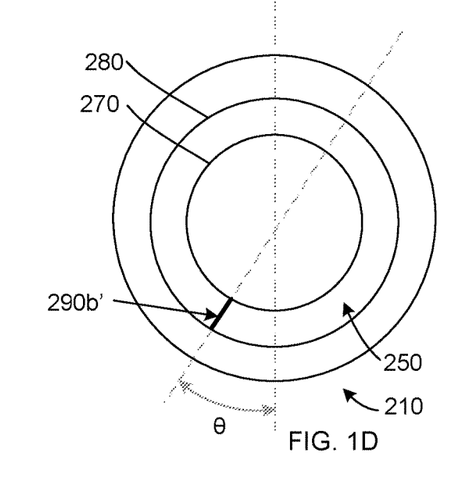
FIG. 1D illustrates a schematic sectional view of the single-start screw-type assembly of FIG. 1C, taken along section B-B, in accordance with an embodiment of the present invention.

FIGS. 1C and 1D provide analogous schematic views of the same illustrative screw-type assembly; however, this system has undergone some amount of plastic deformation and, as a result, shows signs of wear in its present condition. Here, FIG. 1D provides a schematic sectional view of FIG. 1C, taken along section B-B. The illustrative schematic of FIGS. 1C and 1D show a used screw type-assembly that is primarily characterized by a change in radial location of internal start 290b. This parameter is denoted as internal start 290b' and is offset radially from the first radial position of internal start 290b by a deformation angle $\theta$, as shown in FIG. 1D. The used/worn system of FIGS. 1C and 1D may exhibit changes in geometry to at least one or more of the parameters that define internal threads 210, which may include a root 230', a crest 240', a flank 250', a pitch 260', and a thread angle $\alpha'$.

Internal threads 210 in particular are subject to wear that manifests as plastic deformation of its components, including, but not limited to, the radial position of the internal start 290b. This plastic deformation results in localized changes along internal threads 210. External threads 200 are subject to similar wear, although the associated plastic deformation has been found to be less prevalent for external thread components. Such clamping assemblies typically include a handle which is used to tighten the clamp assembly to achieve the aforementioned maintained positive positioning of the overall surgical apparatus. This wear on the threaded components changes the angular positioning of the handle—particularly when the handle is in the tightened position (that which achieves maintained positive positioning of the overall surgical apparatus). The angular positioning of the handle is important; improper angular positioning at a minimum makes maintaining, releasing, and repositioning more difficult for the surgeon to achieve. Improper angular positioning may cause more drastic problems, such as when the handle abuts nearby components of the surgical apparatus (e.g., the base plate).

These problems involving sterilization and wear of surgical equipment have existed for a long period of time without solution. The problem also involves design and construction involving multiple parts such as, for example, complex rails, tubes and other apparatus secured to an operating table. As a result, a simplified design for surgical equipment for holding a limb, joint, or other body part is desired that reduces these and other disadvantages including the cost of the sterilization and overall time and cost of the procedure.

SUMMARY OF THE INVENTION

It is an object of the apparatus, system, and method of the present invention to provide a carriage for positioning an extremity holder having an adjustable cross nut to provide for continued adjustment of the clamping assembly as the associated threaded components wear over time.

It is an object of the apparatus, system, and method of the present invention to provide a carriage for positioning an extremity holder having an adjustable cross nut to provide for replacement of the internal thread component(s) and/or external thread component(s) as these associated threaded components wear over time.

It is an object of the apparatus, system, and method of the present invention to provide a carriage for positioning an extremity holder featuring two locking points achieved by one locking mechanism that is an improvement to prior designs in functionality and holding strength; in particular, as the associated threaded components wear over time.

It is an object of the apparatus, system and method of the present invention to provide a extremity holder such as for a positioning a knee for surgery utilizing a locking the ball and carriage on the fly with a one arm lock and ergonomic handle, where the handle maintains an optimal angular position upon tightening; in particular, as the associated threaded components wear over time.

It is an object of the apparatus, system and method of the present invention to provide a carriage having advantages of minimum parts so as to improve use, sterilization, maintenance thereof.

It is an object of the present invention to provide an apparatus, system and method of treatment that advantageously is rugged in structure and provides support for the patient's limbs or body during the preparation for surgery, when it is necessary to have an extremity draped and available for operation.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Description of the Embodiments, which is to be read in association with the accompanying drawings, which are incorporated in and constitute a part of this specification, show certain aspects of the subject matter disclosed herein and, together with the description, help explain some of the principles associated with the disclosed implementations, wherein.

DESCRIPTION OF THE EMBODIMENTS

Non-limiting embodiments of the present invention will be described below with reference to the accompanying drawings, wherein like reference numerals represent like elements throughout. While the invention has been described in detail with respect to the preferred embodiments thereof, it will be appreciated that upon reading and understanding of the foregoing, certain variations to the preferred embodiments will become apparent, which variations are nonetheless within the spirit and scope of the invention.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Reference throughout this document to "some embodiments", "one embodiment", "certain embodiments", and "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

The drawings featured in the figures are provided for the purposes of illustrating some embodiments of the present invention, and are not to be considered as limitation thereto. Term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein and use of the term "means" is not intended to be limiting.

As used herein the term "adjustable cross nut" refers to a removeable insert having internal threads that is installed into a non-threaded hole (also known as a through hole, or thru-hole); once installed, it is then possible to insert a bolt or threaded rod into the adjustable cross nut; the adjustable cross nut also has at least one "internal start", positioned at a discrete radial location with respect to the central axis of the adjustable cross nut, where the cross nut may be adjusted such that the "internal start" is then positioned at a different discrete radial location with respect to the central axis of the adjustable cross nut.

As used herein the term "body" "body part" "extremity" or "limb" refers to a body part or extremity consisting of foot, ankle, knee, leg, hand, wrist, arm and shoulder of a patient.

As used herein the term "clocking" or "clock" refers to adjusting an adjustable cross nut such that the at least one "internal start" is moved radially from a first discrete radial location to a second discrete radial location and made lockable so that the internal start maintains the second discrete radial location when the system is subject to forces corresponding to a clamping action.

As used herein the term "flash" sterilization is defined as steam sterilization of an unwrapped object at 132° C. for 3 minutes at 27-28 lbs. of pressure in a gravity displacement sterilizer as pioneered by the Underwood and Perkins. Currently, the time required for flash sterilization depends on the type of sterilizer and the type of item, i.e., porous vs non-porous items. Although the wrapped method of sterilization is preferred for the reasons listed below, correctly performed flash sterilization is an effective process for the sterilization of critical medical devices. Flash sterilization is a modification of conventional steam sterilization (either gravity, pre-vacuum, or steam-flush pressure-pulse) in which the flashed item is placed in an open tray or is placed in a specially designed, covered, rigid container to allow for rapid penetration of steam.

As used herein the term "holder" or "extremity holder" refers to a device or a means for supporting the body part, or joint thereof, of a patient in the preparation for surgery or medical activity and/or during surgery to hold a body part for access to the body part. A holder can be used to position the body part such as an arm or leg for patient preparation.

As used herein the term "patient" refers to any recipient of health care services. The patient is most often ill or injured and in need of treatment by a surgeon, physician, physician assistant, advanced practice registered nurse, veterinarian, or other health care provider.

As used herein the term "medical activity" refers to the provision of medical care consisting of hospital activities, medical and dental practice activities, and "other human health activities" by a surgeon, physician, physician assistant, advanced practice registered nurse, veterinarian, or other health care provider. "Medical activity" can also include to numerous activities of medical treatment, diagnosis, preparation for surgery, or inspection of a body part so as to hold a body part for access to the body part.

As used herein the terms "surgery", "operation" "surgical procedure" or refers an act of performing surgery such as by a surgeon, or simply to investigate and/or treat a pathological condition such as disease or injury, or to help improve bodily function or appearance using operative manual and instrumental techniques on a patient to in the medical specialty context. The adjective surgical means pertaining to surgery; e.g., surgical instruments or surgical nurse. The patient or subject on which the surgery is performed can be a person or an animal.

Figure 2:
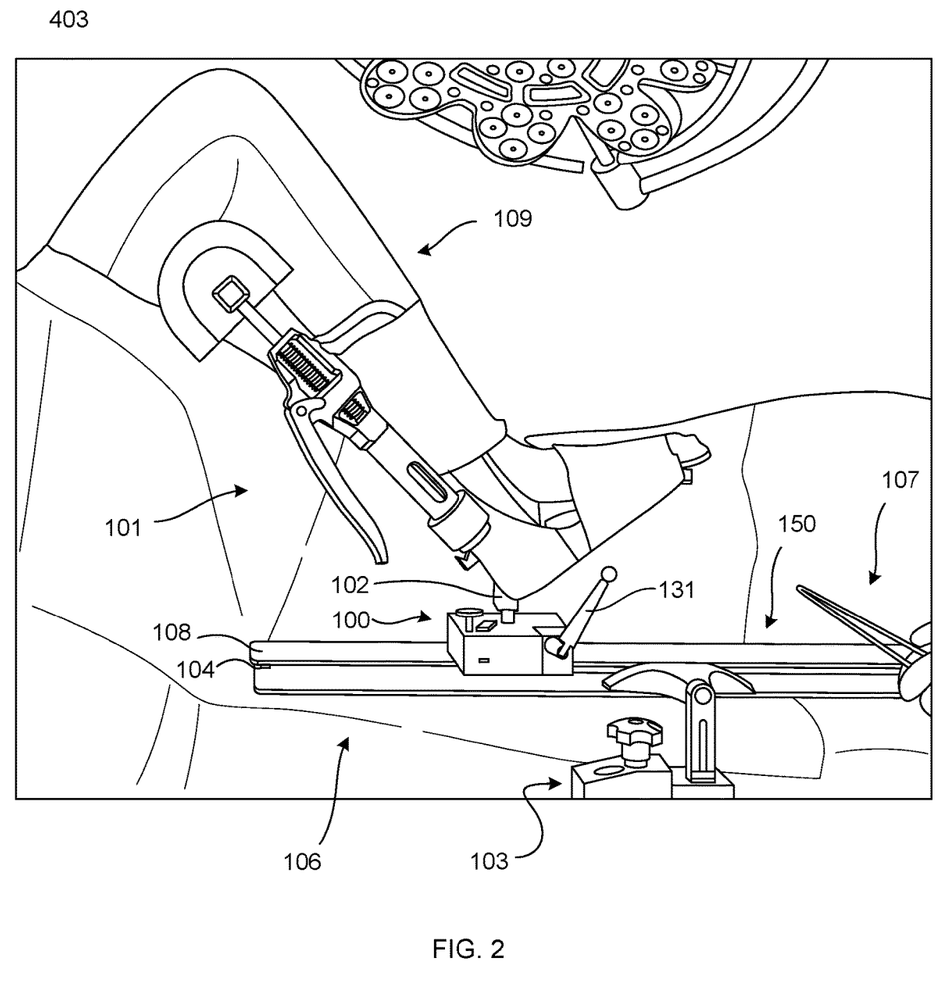
FIG. 2 illustrates a perspective view of a carriage and an adjustable cross nut assembly, an extremity holder, a baseplate having a track, and a clamp disposed on a conventional operating table having side rails, in accordance with an embodiment of the present invention.

Referring to FIGS. 1A-1D through 15A-15F, an apparatus, system and method of assembly of an apparatus for securing an extremity holder to a track secured an operating table useful for performing a surgical procedure using the apparatus, generally shown as element 100, according to an exemplary embodiment of the present invention. FIG. 2 provides an exemplary, full-assembled arrangement of an extremity holder 101 coupled to an apparatus 100, where apparatus 100 is fixedly attached to a track 108 of a base plate 150. Base plate 150 may be disposed on an operating room (OR) table 106 (shown in FIG. 2 with sterile covering), where base plate 150 is coupled to side rail clamp 103, which in turn, is clamped to a side rail (not shown) of OR table 106. Extremity holder 101 of a pre-determined shape is attached to a post 102 at a proximate end and the post 102 has, at a distal end, a ball (not shown) secured at least partially within apparatus 100. In this way, apparatus 100 provides simultaneous locking of two points—extremity holder 101 via ball (not shown) and at a discrete location along track 108—achieved by one locking mechanism, partially shown in FIG. 2 at handle 131. The operating table 106 can have a track 108 as shown in FIG. 2, either integral or attached to the operating table 106 for example, the track 108 is integral to a base plate secured to the operating table 106, for positioning the extremity holder 101 thereby positioning a body part 109 for the surgical procedure.

Figure 9:
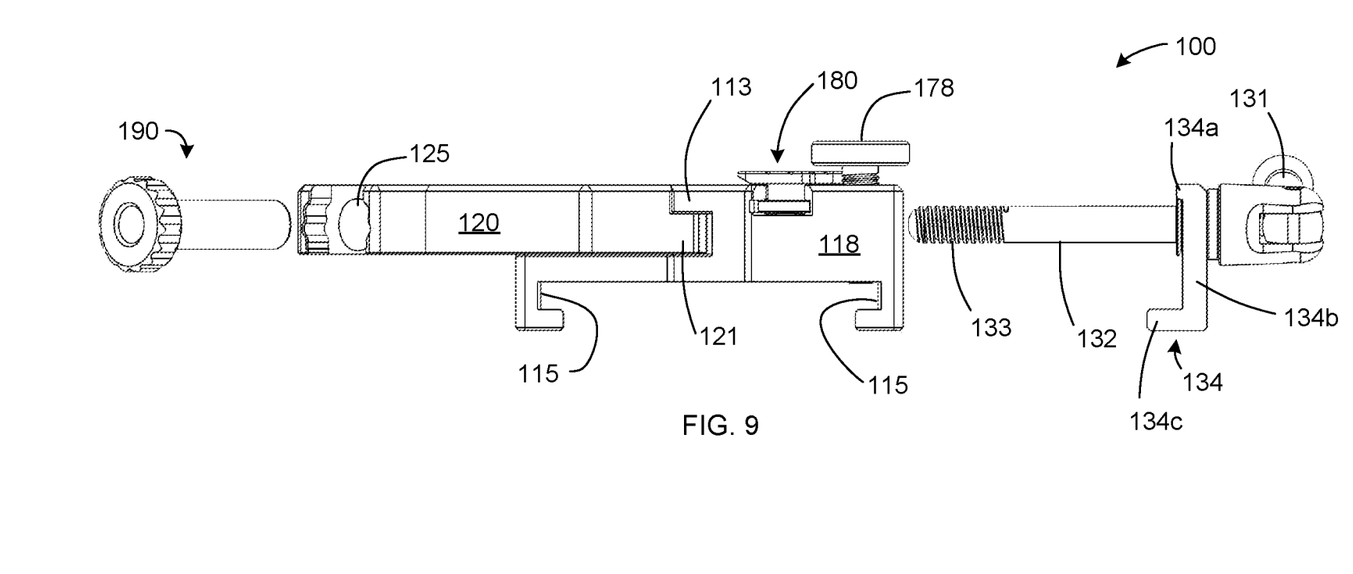
FIG. 9 illustrates another side, partially-exploded view of the apparatus in accordance with an embodiment of the present invention.

Referring to FIGS. 1A-1D through 15A-15F, the apparatus 100 comprises a carriage assembly 110 for supporting the extremity holder 101 on the track 108 and for selective movement of the carriage assembly 110 there along. The carriage assembly 110 and has a base 111 defining a rigid rectangular structure with a step 112. The base comprises a hinge portion 113 having a first knuckle 113a, located at one end of the step 112 for joining an arm 120 thereto and a recess portion 114 located along said step 112 configured to accept a protrusion 127 on arm 120. The base 111 further comprises a track portion 115 defining rails to attach to the track 108, or to a track 108 operably connected by an extendable track 155 thereof, as shown in FIG. 9A.

The base 111 has surfaces of an upper surface 116, lower surface 117 and side surfaces 118. The upper surface 116 is configured with the step 112 generally located and centered along a mid-line, the hinge portion 113 is located at one end of the step 112, and the recess 114 located at another end of the step 112. The track portion 115 is located on a lower surface 117 of the base 111. The base 111 has side surface(s) 118 so as to define a rigid rectangular structure, which is non-limiting as other designs are possible. Because the base 111 is intended for use in an operating room environment, it is formed from materials that are durable, sturdy, and that can be repeatedly sterilized such as, for example, most commonly formed from stainless steel that is known to reduce bacterial and early bio-film attachment, other suitable metals and metal alloys. The base 111 has an opening 119 in a side surface 118 configured to accept a rod 132 of a clamp assembly 130 as is described herein.

The apparatus 100 of the present invention further comprises an arm 120 having a first arm side 120a having an arm hinge portion 121 with a second knuckle 121a and an opening 122 formed as a hole configured to operably receive a pin 123 to join the arm 120 to the base 111. The arm 120 is configured to fit to the base 111 adjacent the step 112 whereby the hinge portion or second knuckle portion 121a aligns with the hinge portion 113 or first knuckle 113a on the base so as to be attached with pin 123, thereby opening and closing of the arm 120 by rotation around the pin 123. The first and second knuckle, 113a and 121a can include a sleeve bearing 124 to provide smooth rotation around the point formed by the hinge portions and pin 123. The arm 120 can be a general rectangular shape and formed from a solid material. A suitable material to form the arm 120 is stainless steel yet other materials and/or metal alloys with qualities of durability, strength and that can be repeatedly sterilized to reduce bacterial attachment can be utilized.

Figure 3:
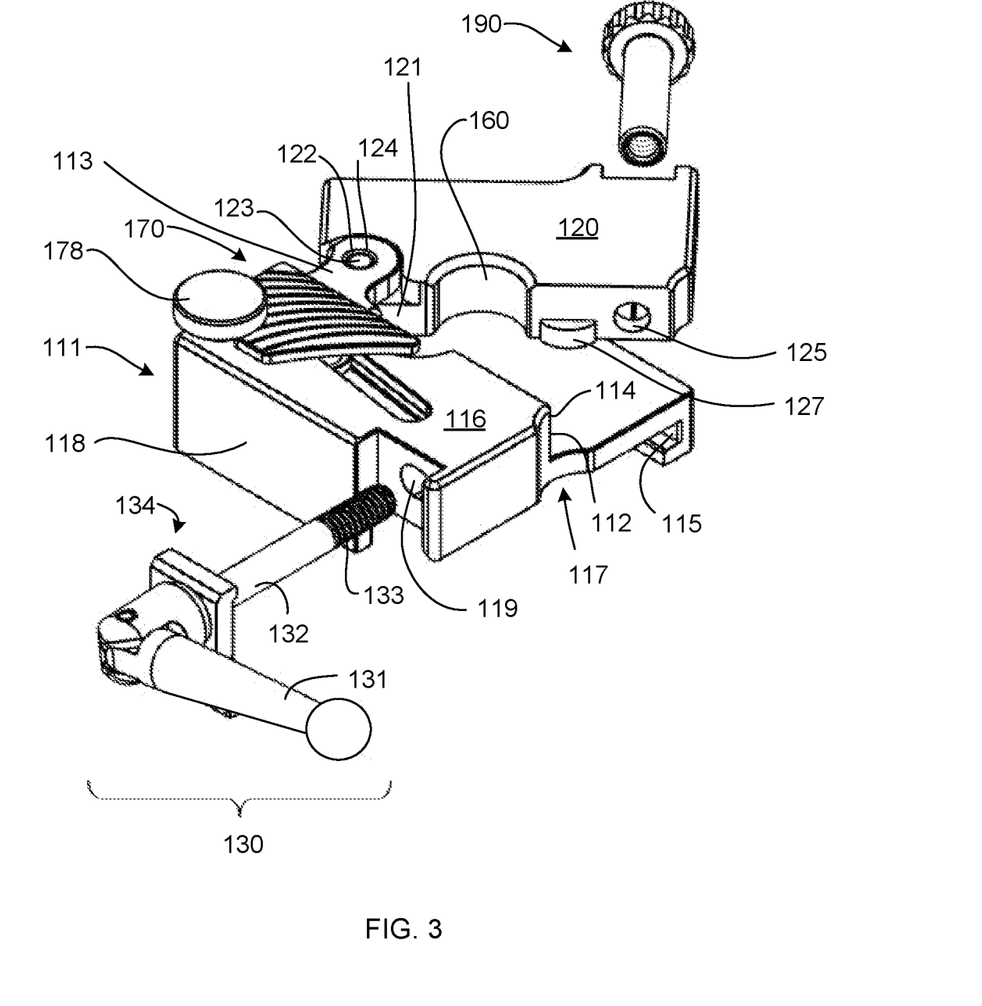
FIG. 3 illustrates a top, prospective, partially-exploded view of the apparatus, system, and method in accordance with an embodiment of the present invention.

As shown in FIG. 3, the arm 120 may be configured with a hole 125 adapted to receive an adjustable cross nut 190, configured to tighten the clamp assembly 130 and perform the holding, securing, and clocking feature(s) of the present invention. The adjustable cross nut 190, in conjunction with features of the carriage assembly 110, generally provide for clocking of the apparatus 100, as will be further detailed below. The arm 120 is further configured with a protrusion 127 adapted to fit to the recess 114 in base 111 adjacent the step 112 by closing the arm 120. The arm 120 is further configured with a sleeve head receiver 128, disposed on a second arm side 120b, as will be further detailed below.

As shown in FIGS. 1A-1D through 15A-15F, the assembly 100 of the present invention is adapted to secure and to hold the extremity holder 101 in a desired position, thereby positioning a body part 109 for a desired surgical procedure 107. The carriage 110 is configured with a socket 160 formed at a mid-point in the upper surface 116, adapted to receive a ball or other attaching means of the extremity holder 101. The socket 160 is formed between the base 111 and arm 120 in the closed position. As the arm 120 abuts the step 112, the protrusion 127 is inserted in the recess along the step 112, thereby creating strength and proper alignment with respect to the holding of the ball. The socket can be tightened or loosed to open and close upon the ball by the clamping action of the clamp assembly 120. For example, a tightening operation involves turning the handle 131 in a particular direction which pulls the arm 120 by engaging a threaded portion 133 of the threaded insert 126 in the hole 125 of the arm 120 with the threaded portion 133 of rod 132. The base 111 and arm 120 are joined and form a fulcrum at the hinge formed by the pin 123 and hinge portions 113, 121, thereby tightening the hold around the ball 105 in the socket 160. A loosening operation involves turning the handle 131 in a particular direction opposite the tightening direction, thereby releasing the hold around the ball in the socket 160 by the similar action of the threads pushing the arm 120 outwardly by the action of engaging the threads of the threaded portion 133 and adjustable cross nut assembly 190.

Figure 11:
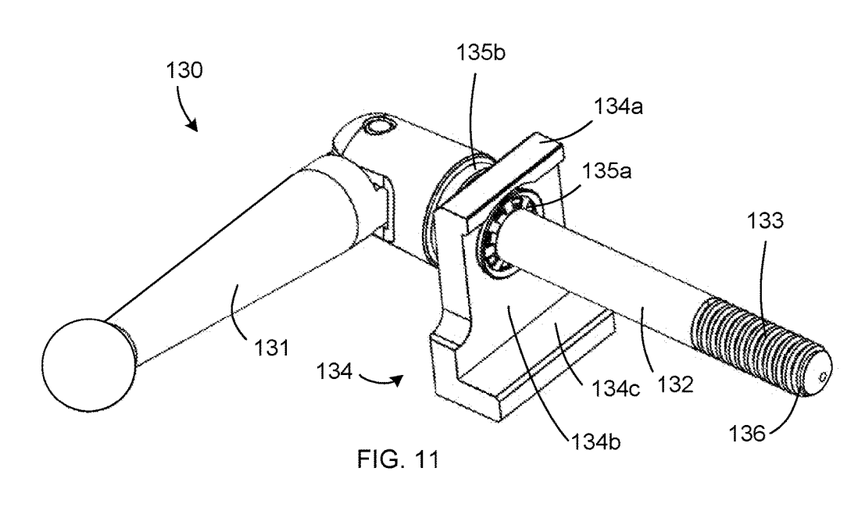
FIG. 11 illustrates a perspective view of a clamp assembly according to an embodiment of the present invention.

As shown in FIGS. 1A-1D through 15A-15F, a clamp assembly 130 may be configured with a handle 131, a rod 132, a track clamp assembly 134, a retaining washer 135a, and a PEEK washer 135b. The handle 131 may be made from stainless steel and have an ergonomic design suitable to provide tightening and improved operation in a user's hands. The rod 132 may similarly be made from made from stainless steel, and may have a threaded portion 133 having an external thread start 136. Rod 132 is configured to be received within opening 119 as demonstrated in at least FIGS. 3-9. As provided in FIG. 6 specifically, opening 119 may take the form of a slotted opening to facilitate proper aligning of rod 132 and adjustable cross nut assembly 190, which reduces the potential for cross-threading and associated damage. Regarding the threaded portion 133, there may be a single external thread start 136 having geometric parameters as shown in FIG. 1A-1D, where (among other components) external thread start 136 corresponds to thread start 290a. Alternatively, apparatus 100 may use thread designs which employ a plurality of thread starts. Track clamp assembly 134 may include an upper track clamp portion 134a, a middle track clamp portion 134b, and a lower track clamp portion 134c, as shown in FIG. 11. The upper track clamp portion 134a may be used to provide the track clamp assembly 134 with the ability to pivot (i.e., to rotate in the x, y, or z directions) to facilitate locking of the carriage assembly 110 onto the track 108. The middle track clamp portion 134b couples to a portion of the vertical surface of track 108, to facilitate clamping and maintaining a localized position of apparatus 100 with respect to the adjacent components while in use, as demonstrated in FIG. 2. The lower track clamp portion 134c may be provided to keep the apparatus 100 from sliding off of either end of track 108; this is accomplished through the use of a spring pin 104 (See FIG. 2), which is configured to abut lower track clamp portion 134c.

In addition, as detailed above, clamp assembly 130 may include a retaining washer 135a, and a PEEK washer 135b disposed on either side of track clamp assembly 134 along rod 132. A retaining washer 135a may have small fins (as illustrated in FIG. 11) that may fit into a groove around rod 132 of the threaded rod that snap into place and keep the entire assembly together. Furthermore, retaining washer 135a may be an off-the-shelf washer that may be installable and precisely position, or otherwise fitted, by the manufacturer. The PEEK washer 135b may be made of polyether ether ketone (PEEK), or a material that exhibits similar material properties, which may be especially adapted for high-stress applications. The PEEK washer 135b may further be adapted to provide uniform load distribution characteristics without causing damage to adjacent surfaces. Additionally, the PEEK washer 135b may also help ensure that the fastener head is pressed against the smooth surface(s) of adjacent part(s) to reduce the chances of it loosening over time.

Each component of the clamp assembly 130 is selected and designed to be easily sterilized for surgical applications. The track clamp tab 134 is used to secure and hold the position of the carriage 110 the track 105 by a compression friction fit in the operation of tightening of the clamp assembly 130. As above, the clamp assembly 130 operates in conjunction with the base 111 and arm 120 as joined at the hinge (the pin 123 and hinge portions 113, 121) to form a fulcrum to tighten and loosen the hold around the ball in the socket 160 that may include an opening 166 formed in the base 111 for improved clearance of tissue and/or fluids and/or sterilization.

Figure 10A:
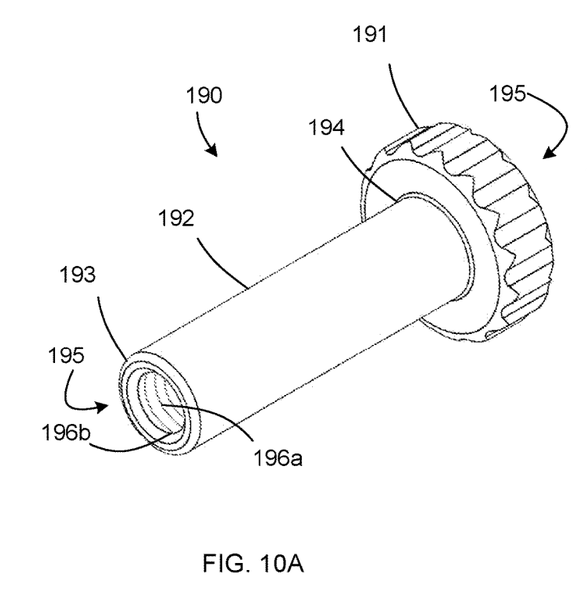
FIG. 10A illustrates a perspective view of an adjustable cross nut assembly in accordance with an embodiment of the present invention.
Figure 10B:
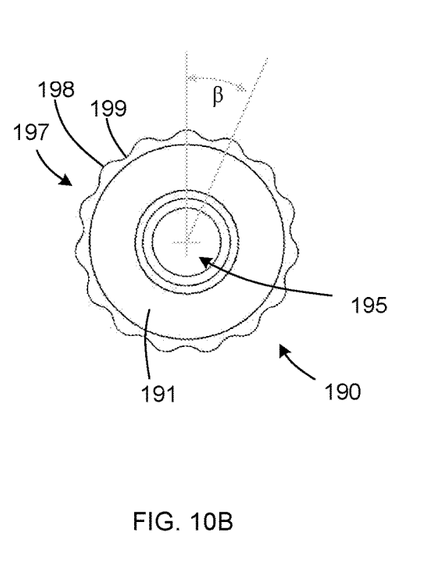
FIG. 10B illustrates a side view of an adjustable cross nut assembly in accordance with an embodiment of the present invention.

Referring now to FIGS. 10A and 10B, an adjustable cross nut assembly 190 is shown, configured to receive the threaded portion 133 of rod 132. Adjustable cross nut assembly 190 may include a sleeve body 192 and a sleeve head 191. Sleeve body 192 is configured to be received within the opening 125 formed within arm 120, as demonstrated in at least FIGS. 3-9. Sleeve body 192 may be formed substantially cylindrical in shape, as shown in FIG. 10A, or in any other extruded shape that facilitates the objective of serving as a cross nut with adjustable clocking capabilities. Sleeve body 192 may extend from a first sleeve end 193 to a second sleeve end 194, and may have a sleeve opening 195 extending therebetween. Sleeve opening 195 comprises a thread engagement portion 196a and at least one internal thread start 196b (as, for example, shown in FIGS. 1A-1D as internal start 290b, 290b'). Also, sleeve opening 195 may extend beyond the plane formed by the second sleeve end 194, such that opening 195 extends longitudinally throughout the entirety of the adjustable cross nut assembly 190, thereby increasing access to thread engagement portion 196a to promote proper sterilization of the adjustable cross nut assembly 190. As to sleeve head 191, it may include sleeve opening 195, as well as at least one rotational inhibitor assembly 197. The at least one rotational inhibitor assembly 197 may include a peak 198 and a trough 199. In an embodiment where adjustable cross nut assembly 190 comprises a plurality of rotational inhibitor assemblies 197, the angle between two adjacent peaks 198 may be defined as angle β. As provided in FIG. 10B, in one embodiment, adjustable cross nut assembly 190 includes 15 discrete rotational inhibitor assemblies 197, yielding β=360°/15=24°. As detailed below, the quantity, placement, and/or shape (i.e., geometry) of rotational inhibitor assemblies 197 is unlimited, and may take any form suitable for achieving clocking of the adjustable cross nut assembly 190. In one embodiment, where 15 rotational inhibitor assemblies 197 are utilized (β=24°), the quantity and geometry of the peaks 198 and troughs 199 has been found to be useful for surgeons or other persons who may be wearing thick gloves, as grasping and maneuvering the adjustable cross nut assembly 190 is made easier, especially for clocking or otherwise adjusting the apparatus 100.

Figure 12:
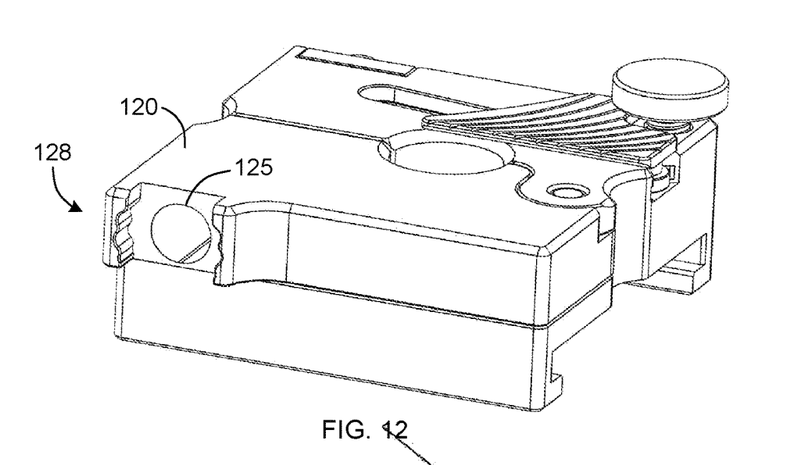
FIG. 12 illustrates a perspective view of a carriage according to an embodiment of the present invention.
Figure 13A:
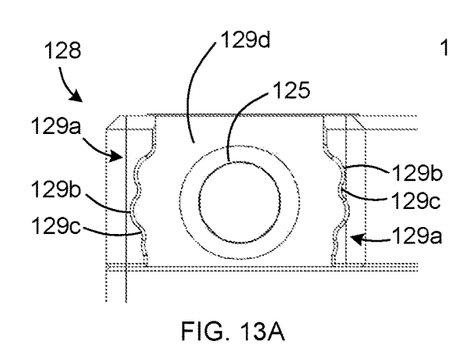
FIG. 13A illustrates a side view of part of a carriage according to an embodiment of the present invention.
Figure 13B:
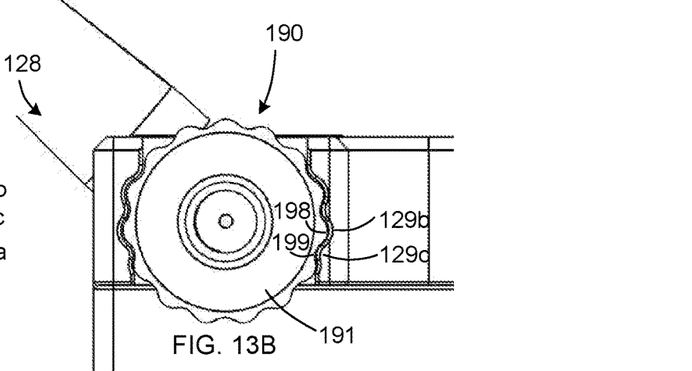
FIG. 13B illustrates a partial side view of part of a carriage and an adjustable cross nut assembly according to an embodiment of the present invention.
Figure 14A:
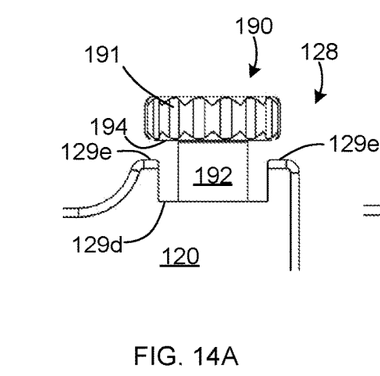
FIGS. 14A, 14B, and 14C illustrate top views of an adjustable cross nut assembly inserted into a carriage at different depths, according to an embodiment of the present invention.

Referring to FIGS. 12 through 14A-14C, a sleeve head receiver assembly 128 is shown. Sleeve head receiver assembly 128, disposed on a second arm side 120b, extends outwardly from arm 120 as shown in FIG. 12, and is configured to receive an adjustable cross nut assembly to facilitate the clamping action of apparatus 100. Sleeve head receiver assembly 128 may include: at least one mirrored rotational inhibitor 129a; a receiver surface 129d disposed at an end, and orthonormal with respect to, opening 125; and a receiver engagement surface 129e, offset from said receiver surface 129d, as shown in FIG. 14A. The at least one mirrored rotational inhibitor 129a includes a mirrored peak 129b and a mirrored trough 129c. As shown in FIGS. 13A and 13B, according to one embodiment, the profile of sleeve head 191 facilitates seating of adjustable cross nut assembly 190 within, or adjacent to, sleeve head receiver assembly 128. Specifically, the at least one rotational inhibitor 197, which includes a peak 198 and trough 199, couples to the at least one mirrored rotational inhibitor 129a, which includes a mirrored peak 129b and a mirrored trough 129c.

FIG. 13B further illustrates how adjustable cross nut assembly 190 may be clocked in accordance with angle β and held, or otherwise maintained, in that angular position by sleeve head receiver assembly 128. The manner in which adjustable cross nut assembly 190 is not limited to the embodiment shown. The at least one rotational inhibitor 197 and corresponding at least one mirrored rotational inhibitor 129a may take any form suited to provide discrete clocking of adjustable cross nut assembly 190 so that the location of the internal thread start 196b may be adjusted to ensure a proper angular location of handle 131 upon tightening and/or achieving the clamping effect. For example, an alternative embodiment may include at least one rotational inhibitor 197 and corresponding at least one mirrored rotational inhibitor 129a formed as a pin-and-hole type rotational inhibitor system. One skilled in the art will recognize that any suitable configuration that provides discrete clocking of adjustable cross nut assembly 190 falls within the scope of this disclosure.

Figure 14B:
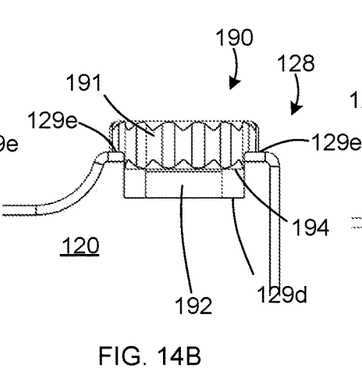
Figure 14C:
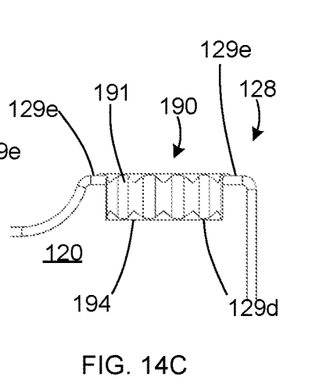

In operation, an adjustable cross nut assembly 190 may provide a clocking function as illustrated in FIGS. 14A-14C. First, as FIG. 14A illustrates, sleeve body 192 of adjustable cross nut assembly 190 may be partially inserted in to opening 125 so that sleeve head 191 may be freely rotatable and clocked as desired. Second, as FIG. 14B illustrates, adjustable cross nut assembly 190 may be further inserted in to opening 125 up until a point where second sleeve end 194 (which also defines an end of sleeve head 191) passes receiver engagement surface 129e in the direction of receiver surface 129d, thus inhibiting rotation of adjustable cross nut assembly 190. Third, clamping assembly 130 may be threaded along threaded portion 133 into thread engagement portion 196a up to a point where second sleeve end 194 couples to receiver surface 129d, which provides the retention, or opposing force, as illustrated in FIG. 14C.

Figure 5:
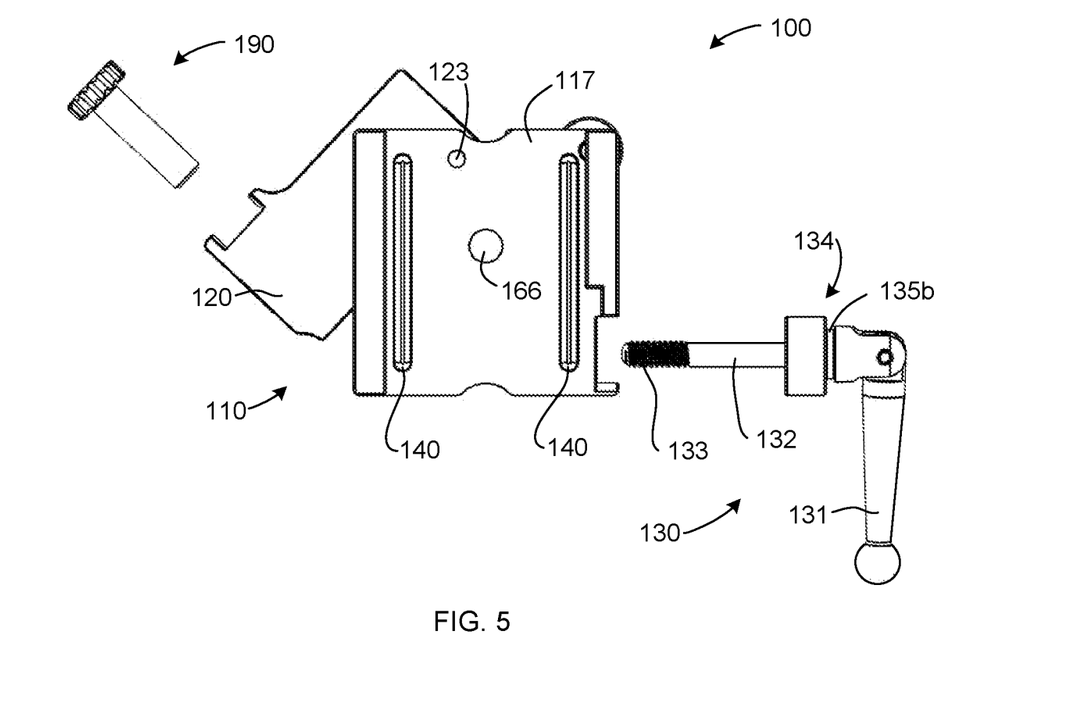
FIG. 5 illustrates a bottom, partially-exploded view the apparatus in accordance with an embodiment of the present invention.
Figure 6:
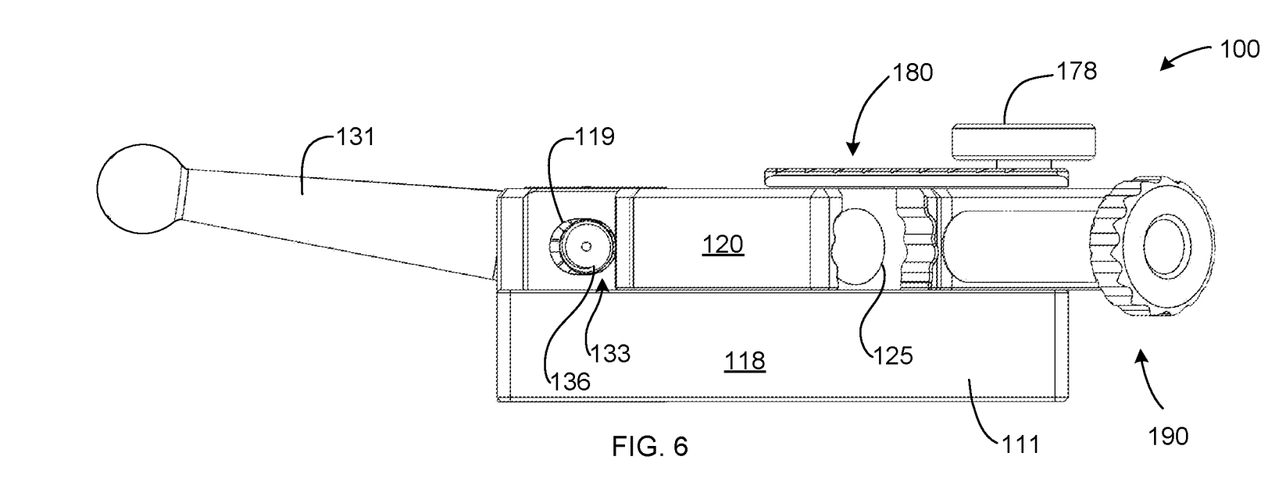
FIG. 6 illustrates a side, partially-exploded view of the apparatus in accordance with an embodiment of the present invention.
Figure 7:
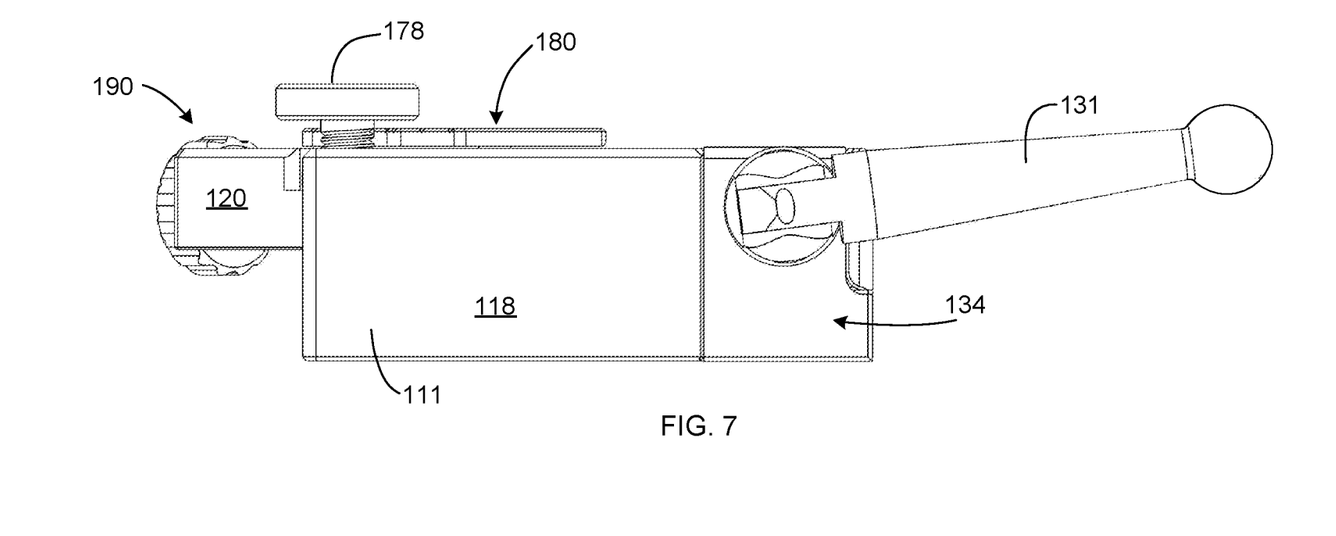
FIG. 7 illustrates another side, partially-exploded view of the apparatus in accordance with an embodiment of the present invention.
Figure 8:
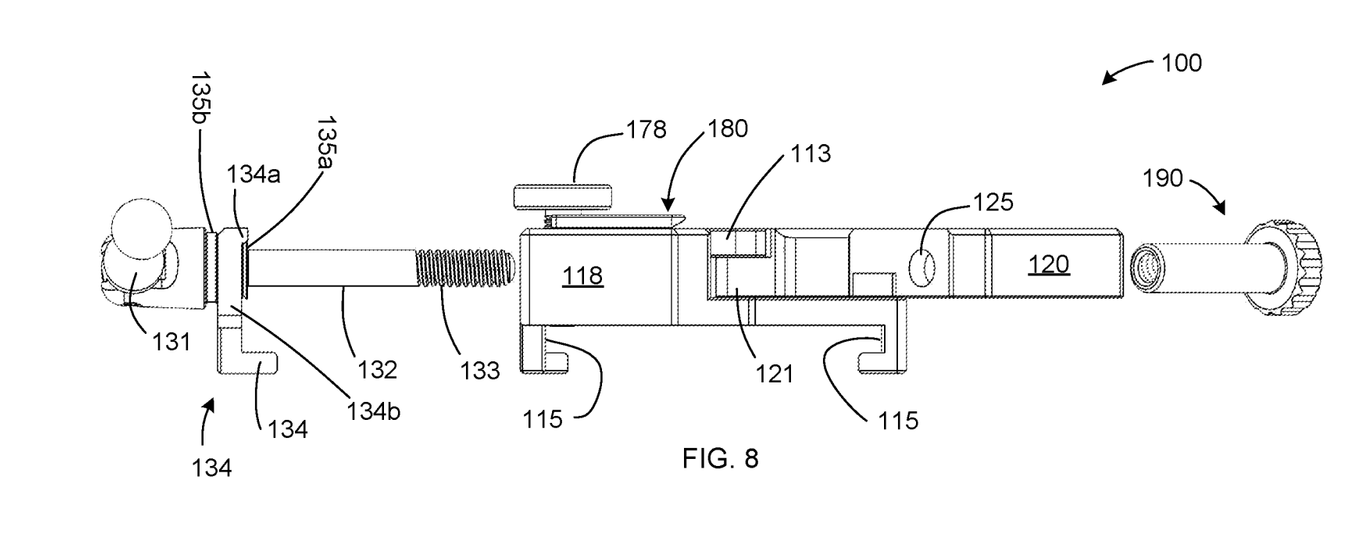
FIG. 8 illustrates another side, partially-exploded view of the apparatus in accordance with an embodiment of the present invention.

As shown in at least FIG. 5, at least one sliding plate 140 may be located between a lower surface 117 of the base 111 and the track 108 for improving sliding movement and positioning of said carriage 110 along the track 108. The at least one sliding plate 140 may be formed of a predetermined friction-reducing material, including a polymer and other materials that can be sterilized. The sliding plate 140 may be formed as a linear strip aligned length-wise to the sliding direction of apparatus 100 along track 108. Alternatively, sliding plate 140 may be formed as a generally planar surface (not shown) shape and tab(s) (also not shown) at one edge configured for placement in holes (not shown) of the base 111. In the alternative embodiment, the sliding plate is configured to pivot between a closed position in a recess in the lower surface 117 of the base 111 when interposed between the base 111 and the track 108 for improving sliding movement and positioning of said carriage 110 along the track 108. The sliding plate then may be pivoted to an open position having the appearance of a flap useful for cleaning and sterilization as well as ease of maintenance and replacement of the sliding plate 140.

Figure 4:
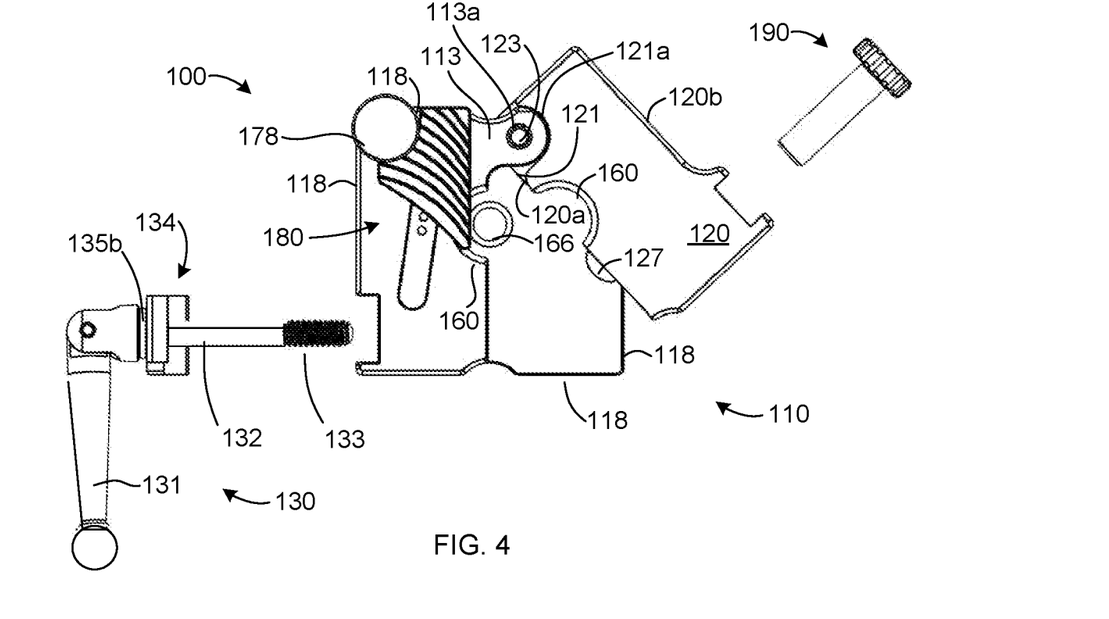
FIG. 4 illustrates a top, partially-exploded view of the apparatus in accordance with an embodiment of the present invention.

Referring now to, for example, FIGS. 3 and 4, carriage assembly 110 incorporates a tilt control assembly 170. The tilt control assembly 170 includes a slide assembly 180 configured to follow a pathway located on the base 111, formed with dimples, which trajectory and dimples can provide predetermined tilt angle(s). According to another aspect of the present invention, a knurled knob 178 may be formed in tilt control assembly 170 to tighten the carriage base 111 to an operating table 106 and prevent movement in all x, y and z directions. The knurled knob 171 is configured to be inserted into a threaded hole in the base 111 so as to set location on the operating table 106, or other track. The knurled knob 171 is configured to lock carriage assembly 100 base 111 anywhere on track thereby forming an "e-brake" and stopping any translational force to assist the clamp assembly 130 with additional locking so as not slide along the rail or track. These parts are minimized for sterilization as the knurled knob 171 requires removal and the hole and knob 171 can be easily cleaned and sterilized.

Figure 15A:
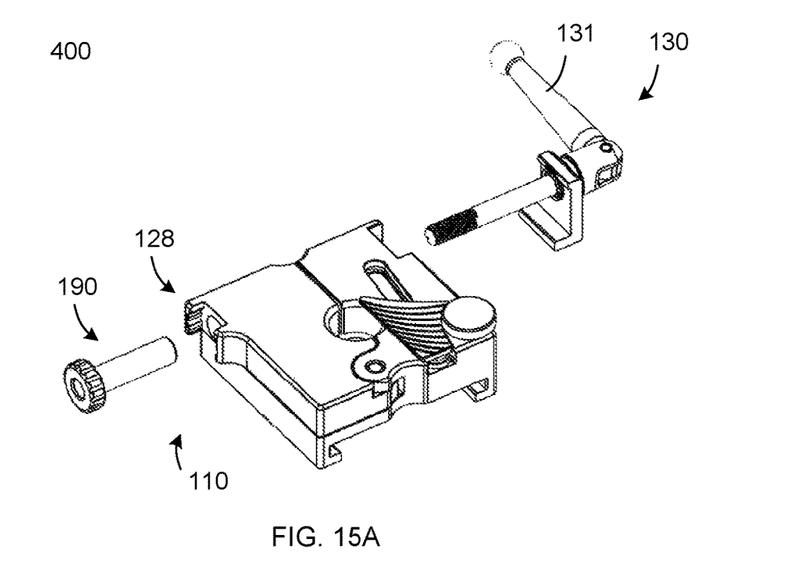
FIGS. 15A, 15B, 15C, 15D, 15E, and 15F illustrate perspective, partially-exploded views of a method of assembling a carriage and an adjustable cross nut assembly according to an embodiment of the present invention.

Referring to FIGS. 15A-15F, a method of assembling an apparatus 100 is described, purposed for securing an extremity holder to a track on an operating table useful for performing surgical procedures. At a first step 400, as shown in FIG. 15A, a carriage assembly 110, a clamping assembly 130, and an adjustable cross nut assembly 190 may be provided. These components may have recently been sterilized, after a previous surgery, or in preparation for an ensuing surgery; apparatus 100 may require clocking to adjust the angular position of handle 131 when in a tightened, or clamped, position. Step 400 may include an initial linear aligning or angular positioning of clamping assembly 130 and adjustable cross nut assembly 190, respectively, with respect to carriage assembly 110.

Figure 15B:
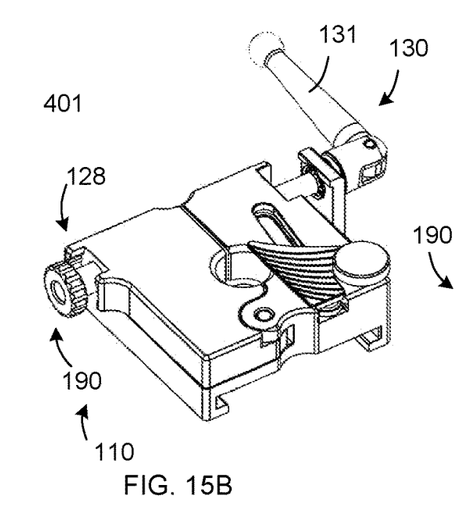
Figure 15C:
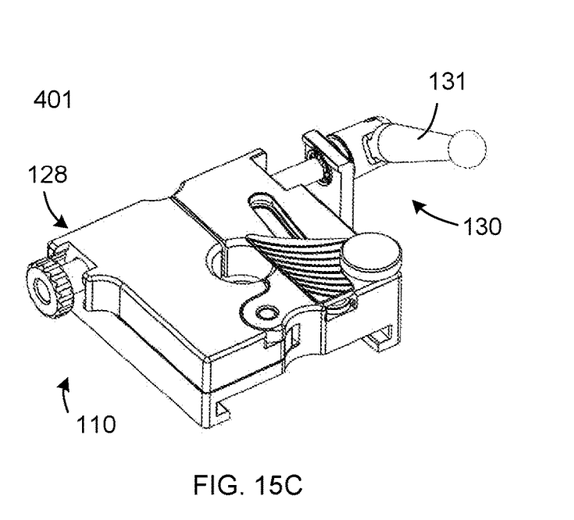
Figure 15D:
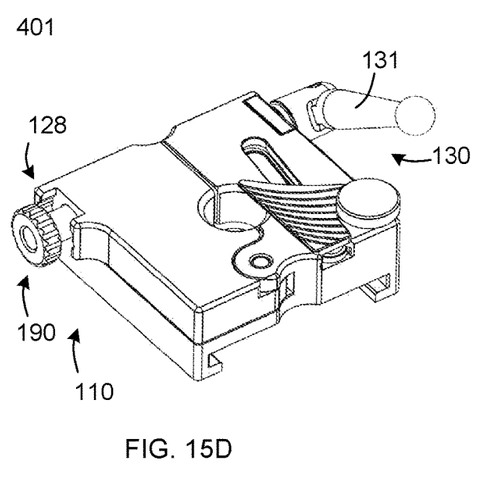

At a second step 401, as shown in FIGS. 15B-15D, clamping assembly 130 and adjustable cross nut assembly 190 are at least partially inserted into openings 115 and 192, respectively. Clamping assembly 130 and adjustable cross nut assembly 190 are then rotated to achieve proper clocking of apparatus 190, so that two locking points (the carriage 110 to the track via track clamp assembly 134, and the carriage to the ball of extremity holder 101 via socket 160) may be effectively achieved by one locking mechanism. Proper clocking may be achieved by adjustable cross nut assembly 190 within sleeve head receiver 128 so that external thread start 136 initially couples to internal thread start 196b and then provides for proper threading of the threaded portion 133 of rod 132 within and along thread engagement portion 196a. Threading of rod 132 is achieved by manipulating, or otherwise rotating, handle 131 while holding adjustable cross nut assembly 190 during this portion of the threading procedure.

Figure 15E:
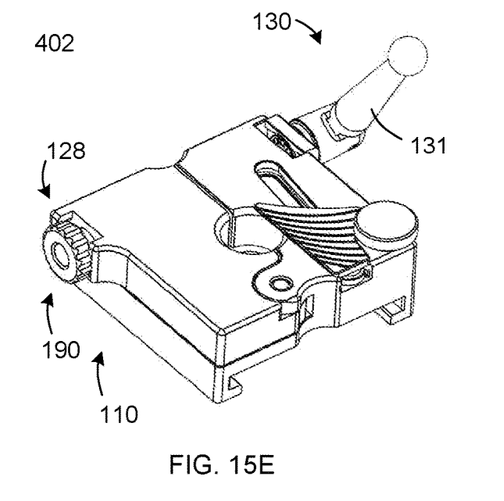

At a third step 402, as illustrated in FIG. 15E, adjustable cross nut assembly 190 is further advanced or inserted in to opening 125 up until a position where second sleeve end 194 (defined as the intersection of sleeve head 191 and sleeve body 192) passes receiver engagement surface 129e in the direction of receiver surface 129d, thus inhibiting rotation of adjustable cross nut assembly 190. This positioning is demonstrated in FIG. 14B. Third step 402 is further characterized in that the carriage assembly may be slidably adjusted along the track 108, and may provide for tilting adjustments of the extremity holder 101 (and ball via socket 160).

Figure 15F:
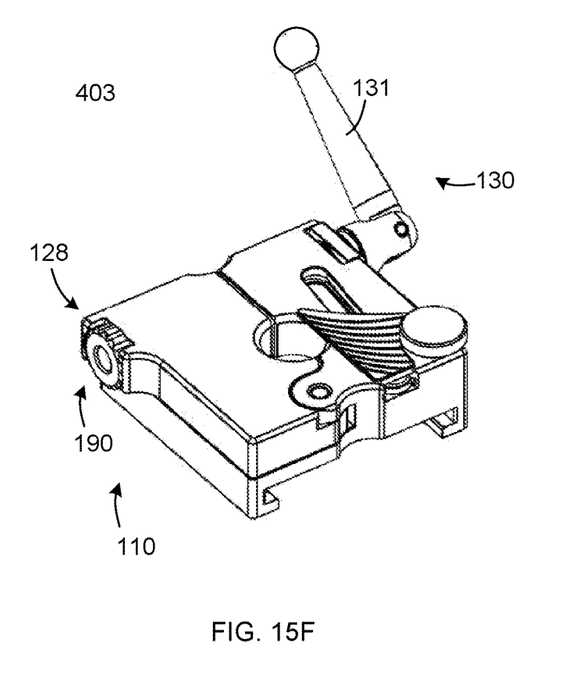

At a fourth step 403, as illustrated in FIG. 15F, adjustable cross nut assembly 190 is further advanced so that second sleeve end 194 couples to receiver surface 129d to provide the retention, or opposing force and rigid clamping facility of apparatus 100, as illustrated in FIG. 14C. Fourth step 403 is further characterized in that carriage assembly is rigidly attached to a discrete location along the track 108, and in that extremity holder 101 (and ball via socket 160) maintains positive positioning with respect to OR table 106. Fourth step 403 is further characterized by the positioning of handle 131, where, when proper clocking of adjustable cross nut assembly 190 is achieved, the handle 131 is positioned substantially as shown in FIG. 15F, and FIG. 2, which provides the optimal positioning and ease of use.

While certain configurations of structures have been illustrated for the purposes of presenting the basic structures of the present invention, one of ordinary skill in the art will appreciate that other variations are possible which would still fall within the scope of the appended claims. Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A carriage assembly for securing an extremity holder to a track of a surgical positioner, said carriage assembly comprising:

a base comprising a body comprising a step formed in an upper surface having a hinge portion, a socket and a recess, and a track portion formed on a lower surface adapted to engage the track with movement therealong, said base having a rod opening located on a side thereof extending through said base to said step, said hinge portion comprising a first knuckle formed at one end of said step, said first knuckle having an opening dimensioned to receive a pin extending through said first knuckle and extending at least partially through said base, and said socket configured to receive a ball joint;

an arm comprising a first arm side having an arm hinge portion, a socket portion, and a protrusion, said arm hinge portion having a second knuckle formed at an end of said first arm side having an opening dimensioned to receive said pin to operably connect to said hinge portion of said base, said protrusion dimensioned to be received in said recess of said base when said arm is in a closed position, said arm further comprising a second arm side having a sleeve head receiver with at least one mirrored rotational inhibitor and a cross nut opening aligned with said rod opening when said arm is in a closed position;

an adjustable cross nut assembly, configured to be received in said cross nut opening, comprising a sleeve body having a first sleeve end with a sleeve opening having a thread engagement portion with at least one internal thread start, said adjustable cross nut assembly further comprising a sleeve head disposed at a second sleeve end of said sleeve body, said sleeve head having a plurality of rotational inhibitors;

a clamp assembly comprising a rod with a first end operably connected to a handle and with a second end having a threaded portion with an external thread start, said rod configured to be received by said rod opening and said second end configured to be received in said thread engagement portion of said adjustable cross nut assembly;

wherein said adjustable cross nut assembly is rotatably adjustable in said sleeve head receiver of said arm such that said at least one mirrored rotational inhibitor is configured to be received by at least one of said plurality of rotational inhibitors of said sleeve head when said arm is in a closed position such that said at least one internal thread start of said sleeve body maintains a first thread start position; and wherein tightening of said handle of said carriage assembly achieves a simultaneous clamping effect of both said track and said extremity holder.

2. The carriage assembly of claim 1, wherein said external thread start of said threaded portion is configured to catch said internal thread start of said thread engagement portion, to begin a threading action to achieve a clamped position.

3. The carriage assembly of claim 1, wherein said adjustable cross nut assembly is rotatably adjustable such that said plurality of rotational inhibitors is configured to be received by said at least one of said mirrored rotational inhibitors on said arm in said closed position such that said internal thread start maintains a second thread start position.

4. The carriage assembly of claim 1, wherein each rotational inhibitor of said plurality of rotational inhibitors further comprises a peak and trough, said plurality of peaks and troughs being radially arrayed about an axis formed by said sleeve opening, each of said peak and said trough configured to be received by a plurality of mirrored rotational inhibitors, each mirrored rotational inhibitor comprising a mirrored peak and a mirrored trough.

5. The carriage assembly of claim 1, wherein each rotational inhibitor of said plurality of rotational inhibitors further comprises a pin, said plurality of pins being radially arrayed about an axis formed by said sleeve opening, each of said pins configured to be received by a plurality of a mirrored rotational inhibitors, each mirrored rotational inhibitor comprising a pin receiver opening.

6. The carriage assembly of claim 1, wherein said sleeve opening extends through said adjustable cross nut assembly.

7. The carriage assembly of claim 1, wherein said rod opening forms a slot to allow adjustments of said rod within said rod opening to provide proper alignment of said threaded portion with said thread engagement portion.

8. The carriage assembly of claim 1, wherein said clamp assembly further comprises a track clamp assembly comprising a retaining washer, a washer, and upper, middle, and lower track clamp portions, said middle track clamp portion having an opening configured for passing said rod therethrough.

9. The carriage assembly of claim 8, wherein said middle track clamp portion is configured to transfer a clamping force from said handle, through said carriage assembly, to said sleeve head when said arm of said carriage assembly is in said closed position.

10. The carriage assembly of claim 8, wherein said upper track clamp portion is configured to pivot said track clamp assembly to achieve proper positioning of said clamping assembly when said carriage assembly is being tightened to achieve a clamping effect.

11. The carriage assembly of claim 8, wherein said lower track clamp portion is configured to keep the carriage assembly from sliding off of either end of said track by abutting a spring pin disposed at each end of said track when said carriage assembly is slidably adjusted thereon.

12. The carriage assembly of claim 8, wherein said washer comprises a high-stress washer configured to uniformly distribute a clamping force transferred from said handle to said middle track clamp portion when said arm of said carriage assembly is in said closed position.

13. The carriage assembly of claim 12, wherein said high-stress washer is made of polyether ether ketone (PEEK).

14. A method of assembling a carriage assembly for securing an extremity holder to a track of a surgical positioner, the method comprising:
  providing the carriage assembly recited in claim 1;
  inserting, at least partially, said sleeve body of said adjustable cross nut assembly into said cross nut opening of said arm;
  inserting, at least partially, said rod of said clamping assembly into said rod opening of said base;
  rotating said adjustable cross nut assembly to align said internal thread start with a first position, by rotating and aligning a first rotational inhibitor of said plurality of rotational inhibitors with a first mirrored rotational inhibitor of said plurality of mirrored rotational inhibitors;
  threading, at least partially, said threaded portion of said rod into said thread engagement portion of said sleeve body such that said sleeve head rotatably locks within said sleeve head receiver of said arm to maintain said first position of said internal thread start;
  positioning said carriage assembly onto said track;
  positioning a ball of said extremity holder into said socket of said carriage assembly; and
  threading said threaded portion of said rod into said thread engagement portion of said sleeve body such that said carriage assembly achieves a simultaneous clamping effect of both said track and said extremity holder.

* * * * *